United States Patent [19]

Clark

[11] Patent Number: 5,013,299
[45] Date of Patent: May 7, 1991

[54] SYRINGE RESHEATHING DEVICE

[76] Inventor: William C. Clark, P.O. Box 2777, Knoxville, Tenn. 37901

[21] Appl. No.: 408,676

[22] Filed: Sep. 18, 1989

Related U.S. Application Data

[63] Continuation-in-part of Ser. No. 164,348, Mar. 4, 1988, abandoned, which is a continuation-in-part of Ser. No. 23,638, Mar. 9, 1987, abandoned, and a continuation-in-part of Ser. No. 28,410, Mar. 20, 1987, abandoned.

[51] Int. Cl.$^5$ .................. A61M 5/38; B65D 85/00
[52] U.S. Cl. .................. 604/114; 604/192; 604/263; 206/366; 248/523; 312/209
[58] Field of Search .............. 604/181, 110, 192, 199, 604/263, 232, 181, 407, 113, 114; 128/396, 397; 248/309.1, 523, 534, 539, 514; 211/13, 60.1; 206/364, 365, 366; 312/209

[56] References Cited

U.S. PATENT DOCUMENTS

| D. 248,491 | 7/1978 | Reiss . |
|---|---|---|
| 881,017 | 3/1908 | Morse . |
| 1,647,039 | 10/1927 | Fisher et al. . |
| 2,393,576 | 1/1946 | Thomas . |
| 2,642,868 | 6/1953 | Pontius . |
| 2,854,976 | 10/1958 | Heydrich . |
| 3,596,659 | 8/1971 | Glaser . |
| 4,040,419 | 8/1977 | Goldman . |
| 4,062,353 | 12/1977 | Foster et al. . |
| 4,185,619 | 1/1980 | Reiss . |
| 4,286,591 | 9/1981 | Raines . |
| 4,629,453 | 12/1986 | Cooper . |
| 4,673,184 | 6/1987 | Oliver . |
| 4,737,149 | 4/1988 | Gillilan . |
| 4,742,910 | 5/1988 | Staebler . |
| 4,753,345 | 6/1988 | Goodsir . |

FOREIGN PATENT DOCUMENTS

| 192453 | 8/1986 | European Pat. Off. . |
|---|---|---|
| 447992 | 8/1927 | Fed. Rep. of Germany . |
| 3215289 | 3/1983 | Fed. Rep. of Germany . |
| 3433359 | 4/1986 | Fed. Rep. of Germany . |
| 572400 | 6/1924 | France . |
| 741025 | 2/1933 | France . |
| 756530 | 2/1934 | France . |

Primary Examiner—Stephen C. Pellegrino
Attorney, Agent, or Firm—Pitts and Brittian

[57] ABSTRACT

A syringe resheathing and holding device (10) for lockably receiving the needle sheath (16) of a hypodermic syringe (20) to permit unsheathing and resheathing using only one hand. The resheathing device (10) comprises a base member (12) for being supported and at least one sheath holder (14). The sheath holder (14) includes sidewalls (22), and a first end portion (24) and a second end portion (26), the first end portion (24) being secured to the base member (12). Further, the sheath holder (14) is provided with a sheath receptor (28) for lockably receiving the needle sheath (16). A suitable locking means is also provided for releasably locking the sheath (16) in the sheath receptor (28) while the syringe is being unsheathed and resheathed.

20 Claims, 5 Drawing Sheets

SYRINGE RESHEATHING DEVICE

This is a continuation-in-part application based upon parent application Ser. No. 164,348 filed Mar. 4, 1988, now abandoned which in turn was based upon parent application Ser. No. 023,638 filed Mar. 9, 1987, now abandoned parent application Ser. No. 028,410 filed Mar. 20, 1987, now abandoned.

TECHNICAL FIELD

This invention relates to a syringe resheathing device for lockably holding the needle sheath of a hypodermic syringe so as to facilitate the unsheathing and resheathing of the syringe using only one hand so as to prevent accidental contact with the needle of the syringe. In this particular invention, the device comprises a base member on which is supported one or more sheath holders, with the sheath holder(s) having means to lock the sheath until it is desired that the sheath be removed.

BACKGROUND ART

In recent years, the rise in the incidence of Acquired Immune Deficiency Syndrome (AIDS), hepatitis, and other blood contaminating infections, has underscored the need for protecting health care workers from contact with contaminated blood and other bodily fluids. In this regard, the risk of contact with contaminated blood or fluid can be substantial during the administering of injections with hypodermic syringes and if great care is not taken, the administering health care worker can be accidentally injected or can otherwise come in contact with a contaminated needle. Of course, by resheathing the hypodermic needle with the needle sheath provided with most conventional syringes, the risk of contact with contaminated fluids can be reduced, but the risk of inadvertent injection or contact with a contaminated needle can be greatest when the manual resheathing of the syringe is attempted. Various devices have been constructed to make the administration of injections safer, but none of them have provided a safe and efficient device for resheathing a contaminated hypodermic needle. For example, in the above referenced applications Ser. Nos. 07/023,638, 07/028,410 and 07/164,348, the Examiner cited the following patents:

| PATENT NO. | DATE | INVENTOR | COUNTRY |
| --- | --- | --- | --- |
| 881,017 | 03/03/08 | W. E. H. Morse | USA |
| 572,400 | 06/1924 | M. Rossi | FRANCE |
| 447,992 | 08/1927 | O. Hirsch, et al. | GERMANY |
| 1,647,039 | 10/25/27 | R. L. Fischer | USA |
| 741,025 | 02/1933 | M. L. Laval | FRANCE |
| 756,530 | 02/1934 | M. Ollivier | FRANCE |
| 2,393,576 | 01/22/46 | G. J. Thomas | USA |
| 2,642,868 | 06/23/53 | O. H. Pontius | USA |
| 2,854,976 | 10/07/58 | S. E. Heydrich | USA |
| 3,215,289 | 03/11/83 | W. Bausch, et al. | GERMANY |
| 3,433,359 | 04/03/86 | S. Kreisz | GERMANY |
| Des. 192,453 | 08/27/86 | R. Law | EUROPE |
| 3,596,659 | 08/03/71 | H. Glasser | USA |
| 4,040,419 | 08/09/77 | A. Goldman | USA |
| 4,062,353 | 12/13/77 | E. Foster, et al. | USA |
| Des. 248,491 | 07/11/78 | J. M. Reiss | USA |
| 4,185,619 | 01/29/80 | J. M. Reiss | USA |
| 4,286,591 | 09/01/81 | K. Raines | USA |
| 4,629,453 | 12/16/86 | T. M. Cooper | USA |
| 4,673,148 | 06/16/87 | J. A. Oliver | USA |
| 4,737,149 | 04/12/88 | J. T. Vernon | USA |
| 4,742,910 | 01/10/88 | C. R. Staebler | USA |
| 4,753,345 | 06/28/88 | S. W. Goodsir | USA |

A further problem that is encountered, particular by those in the dental profession, for example, is the need to administer a plurality of materials via syringe needles. These are usually preloaded with the various materials and placed on a table for ready access. Some materials may be used more than once during a procedure and thus the needle of a syringe will be unsheathed and resheathed a number of times. Further, there is a need for this to be done quickly, efficiently and safely.

A shortcoming of all of the known devices useful for the unsheathing an resheathing of hypodermic syringes is that they require the use of two hands: one to hold the device; and the other to hold the syringe. For example, Kreisz has a body or grip (1) that is held in one hand while the second hand manipulates the syringe needle into and out of the needle sheath. This is true, also, for the device of Vernon (see in particular FIG. 4) where there is a body (29) to be held with one hand while the user inserts or removes the needle with the other hand.

Another shortcoming of numerous of the devices of the prior art is the manner in which the sheath is held in the sheath holder. These depend upon some form of frictional fit. While this can possibly prevent loss of the sheath from the holder, it would be insufficient to prevent loss of a whole syringe and its sheath. Typical of the devices that rely on this "dynamic" engagement are the units of Kriesz, Vernon, Law and Stabler (which issued after the filing of the parent application to this continuation-in-part application). Thus, during transport, as from a storage compartment to a using location, separation could occur inadvertently. Also, there is no assurance that just a friction fit will adequately hold the sheath as the needle is withdrawn therefrom. While Vernon and Kriesz provide a notch to hold a flange of the sheath, in addition to a friction member, a force must be applied that is transverse to the axis of the syringe. This force may cause leakage between the threads on the end of the syringe and the typical plastic hub of the needle. This further emphasizes the need for use of two hands by users of these devices.

Therefore, it is an object of the present invention to provide a resheathing device for releasably locking the needle sheath of a hypodermic syringe to allow the safe resheathing of a contaminated needle.

It is another object of the present invention to provide a resheathing device which serves as a holder for a syringe when the syringe is not in use.

Yet another object of the present invention is to provide a resheathing device which is portable and which includes a means for lockably engaging a syringe during transport to avoid inadvertent unsheathing of the hypodermic needle.

It is also an object of the present invention to provide a structure whereby a user can unsheath and resheath the needle of a syringe using only one hand so as to minimize inadvertent contact with the syringe needle.

A further object of the present invention is to provide a resheathing device which is inexpensive to manufacture and maintain.

DISCLOSURE OF THE INVENTION

Other objects and advantages will be accomplished by the present invention which provides a syringe resheathing device for lockably receiving the needle sheath of a hypodermic syringe. The resheathing device comprises a base member on which is supported at least one sheath holder. The sheath holder includes sidewalls, and defines first and second end portions. Further, the sheath holder is provided with a sheath receptor having an opening at said first end of said holder, for receiving the needle sheath of a syringe. A locking means, passing through a side wall of the sheath holder has a first end within the receptor which is provided for locking the needle sheath in the sheath receptor during the unsheathing and resheathing of the syringe such that the risk of inadvertent injection or contact with the needle is reduced. A second end of the locking means is disposed exterior to the sheath holder for operation by a user to achieve the locking as well as the intentional unlocking of the sheath.

BRIEF DESCRIPTION OF THE DRAWINGS

The above-mentioned features of the invention will become more clearly understood from the following detailed description of the invention read together with the following drawings.

BEST MODE FOR CARRYING OUT THE INVENTION

Figure 1:
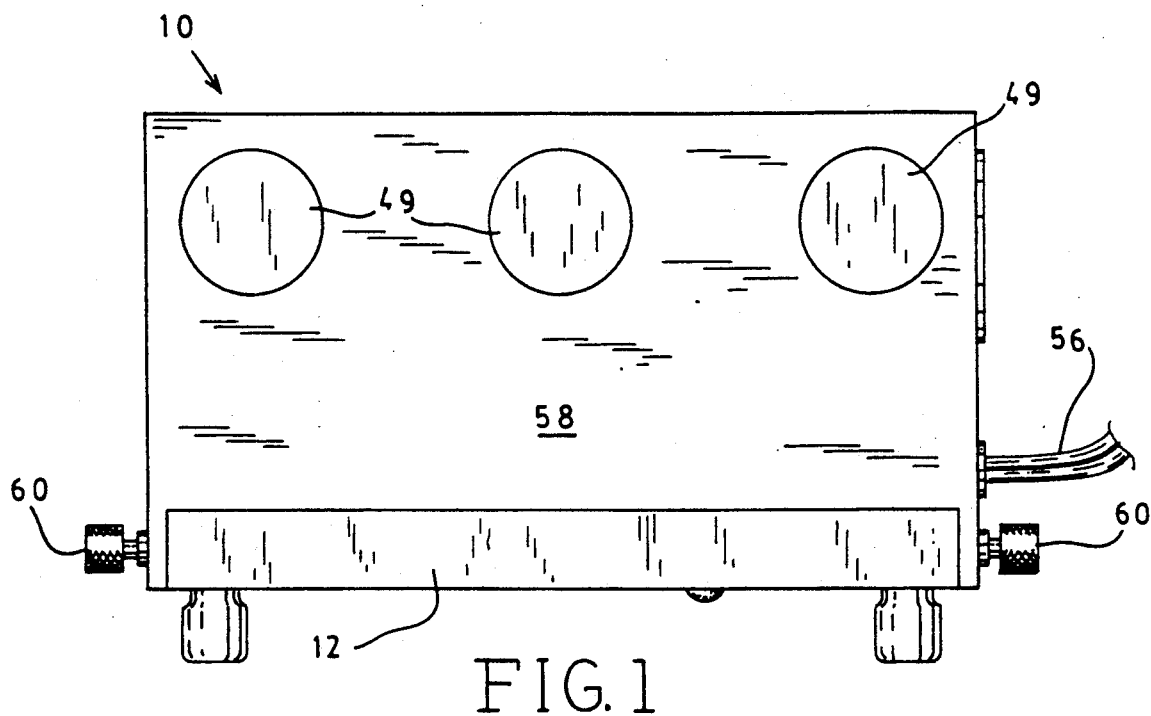
FIG. 1 illustrates a front elevation view of one embodiment of a syringe resheathing device of the present invention.

One embodiment of a syringe resheathing device incorporating various features of the present invention is illustrated at 10 in FIGS. 1-5. The resheathing device 10 generally comprises a base member 12 which supports, on a suitable support surface, one or more sheath holders 14 for lockably receiving a syringe sheath 16 which releasably covers the needle 18 of a conventional hypodermic syringe 20. In this regard, the sheath holders 14 are designed to facilitate the safe unsheathing and resheathing of hypodermic needles using only one hand and to hold a sheathed syringe in a convenient position while the syringe is not in use.

As used herein the term "lock" is meant "to make secure", "hold fast" which is a static engagement operation and one that requires specific action by a user. This is in contrast to dynamic engagement, such as a frictional fit, that does not require action by a user.

Figure 2:
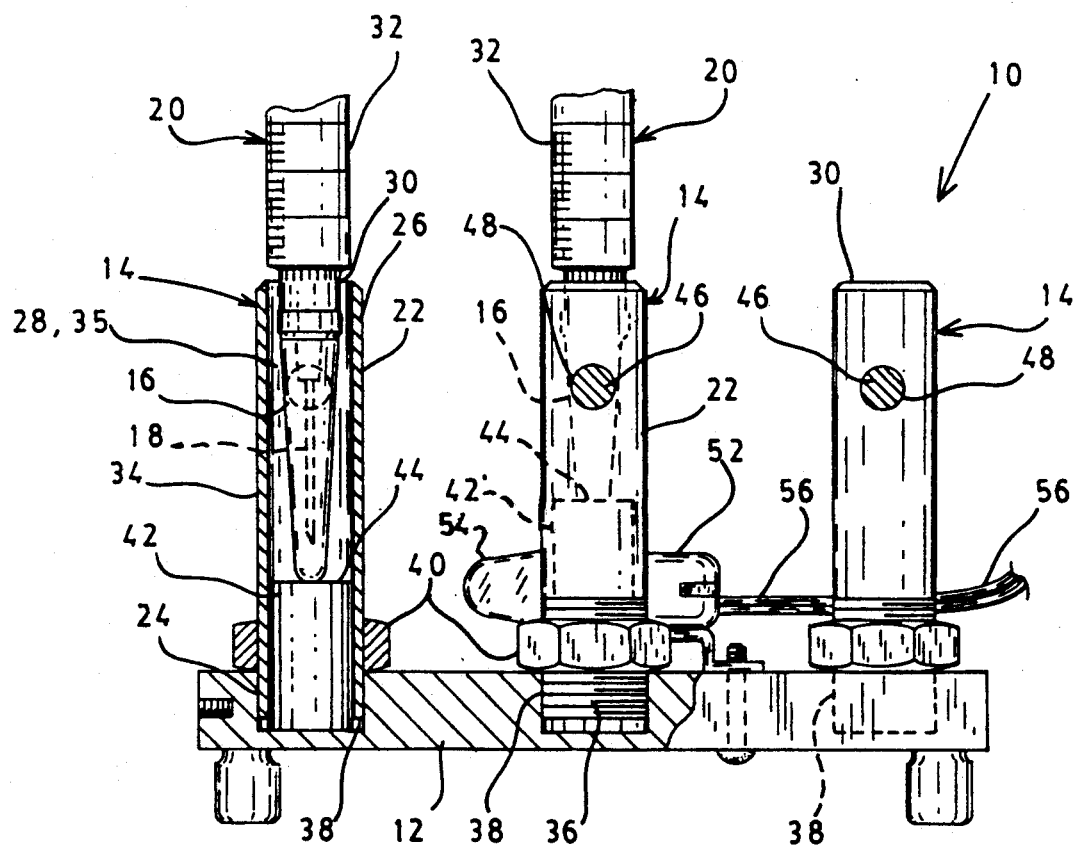
FIG. 2 illustrates a front elevation view, partially in section, of the resheathing device of FIG. 1 with its housing removed.

Referring now to FIGS. 1 through 4, in this embodiment, the device 10 is provided with a plurality of sheath holders 14 mounted vertically on the base member, each of which defines a sidewall 22, and first and second end portions 24 and 26, respectively. Each of the holders 14 is secured to the base member 12 at its first end portion, and defines a sheath receptor 28 accessible through an opening 30 at the second end portion 26 of the holder 14. The receptor 28 of each of the holders 14 is releasably receptive of a syringe sheath 16 as illustrated in FIG. 2. Accordingly, when the sheath 16 is in place over the needle 18 of the syringe 20, the sheath can be inserted into the receptor 28 and the syringe will be held in a convenient downwardly disposed position with the barrel 32 of the syringe exposed for grasping.

It will be noted that in this illustrated embodiment, each of the holders 14 comprises a cylindrical sleeve 34 defining a passageway 35 therethrough, and a first and second end portion corresponding to the end portions 24 and 26 of the holder 14. The first end portion 24 is provided with a threaded exterior portion 36 for being releasably received in a threaded receptor 38 provided in the base member 12. In order to avoid inadvertent rotation of the sleeve 34 in the receptor 38, a locking nut 40 can be provided on the threaded portion 36 which can be downwardly threaded to lock the sleeve 34 in position in the receptor 38. Further, depending upon the length of the syringe sheath 16 to be received by the sheath receptor 28, a spacer member 42 having a preselected length can be inserted into the passageway 35 such that the upper surface 44 of the spacer member 42 defines the bottom of the sheath receptor 28 and, thus, serves to support the inserted syringe sheath 16. For example, in FIG. 2, the spacer member 42 is shorter in length than the spacer member 42' to allow the sheath receptor to accommodate a longer syringe sheath 16.

Figure 4:
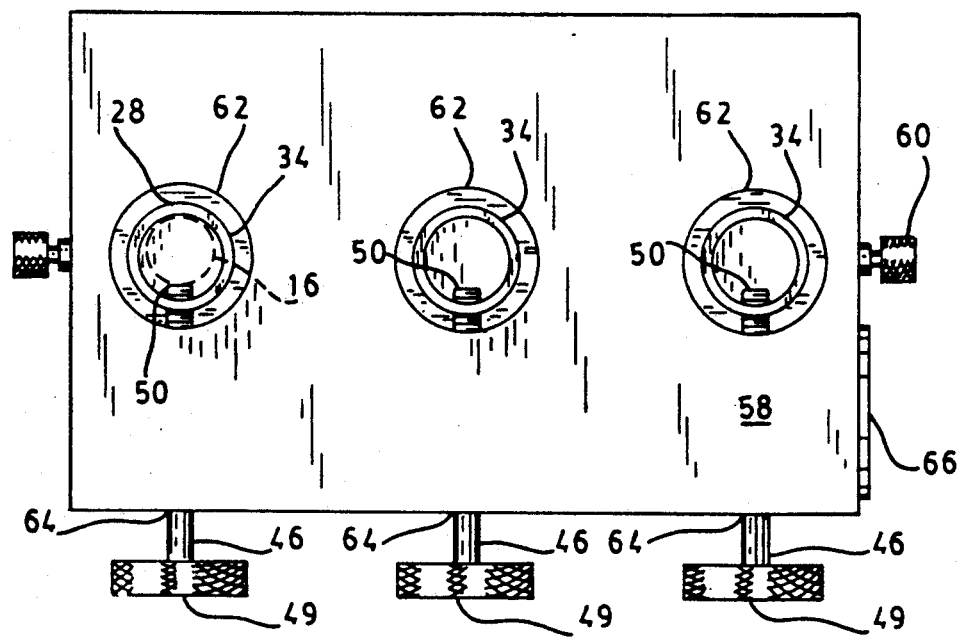
FIG. 4 illustrates a top view of a resheathing device of FIG. 1.

Each of the sheath holders 14 is also provided with locking means for releasably locking a syringe sheath 16 in the receptor 22 such that the sheath 16 is held in place as the syringe 20 is selectively unsheathed and resheathed. In this illustrated embodiment, such locking means comprises a setscrew 46 for being threadably received in a threaded opening 48 provided through the wall of the sleeve 34. The outboard end of each setscrew 46 carries a knob 49, preferably knurled, to facilitate rotation of the setscrew 46 by a user. The second end 50 is within the receptor 28. Accordingly, as illustrated in FIG. 4, the sheath 16 is locked in the receptor 28 by threading the setscrew 46 into the receptor 28 until the inboard end 50 of the setscrew firmly engages the sheath 16. Of course, with the sheath 16 held securely in the receptor 28, the syringe 20 can be unsheathed and resheathed with one hand by safely grasping the barrel 32 of the syringe 20, with no need for the other hand to be placed in a position to be inadvertently injected or otherwise contacted by the needle of the syringe. Further, a resheathed syringe can be removed from the receptor 28 by simply rotating the setscrew 46 to back the inboard end 50 of the setscrew away from the sheath and withdrawing the syringe by the barrel 32. It should be noted that the setscrews 46 merely represent one preferred locking means, and other suitable locking means can be used through the wall of the sleeve 34 to releasably secure a sheath 16 in the receptors 28.

The base member 12 and the various components of the sheath holders 14 are preferably fabricated of brass, surgical steel, or some other strong durable material.

Further, it will be appreciated that the above described construction allows the device 10 to be easily disassembled for cleaning and sterilization. For example, the device 10 can readily be disassembled and its components placed in a conventional autoclave for sterilization. It will also be appreciated that a base member can be provided that mounts the sheath holders at other angles, and also the sheath holders can be secured to the base member at other than the end.

Figure 3:
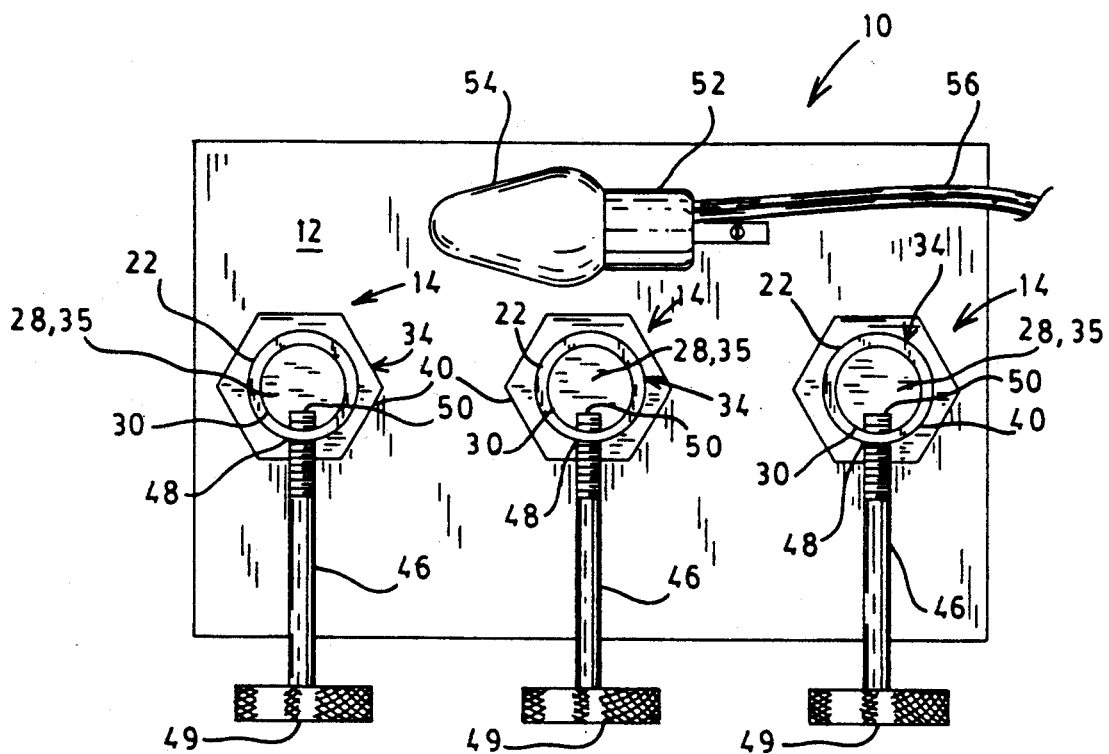
FIG. 3 illustrates a top view of the resheathing device of FIG. 1 with its housing removed.

For some medical procedures, it is desirable for the hypodermic needle, and/or the syringe and its contents, to be warmer than the ambient room temperature. Therefore, as is best illustrated in FIGS. 2 and 3, the preferred embodiment of the device 10 of FIG. 1 also comprises heating means for warming a needle, and/or syringe, which is being held by one of the sheath holders 14. In the illustrated embodiment, such heater means comprises a light bulb socket 52 mounted on the base member 12 for receiving a light bulb 54. The socket 52 is provided with an electrical cord 56 for connecting the socket 52 to a suitable electrical power source. Of course, when illuminated, the light bulb 54 gives off heat which is communicated through to holders 14 to the sheath 16, and to the needle and syringe. Further, the device 10 is provided with a housing 58 which encloses the bulb 54 and socket 52, as well as the sheath holders 14 such that the heat generated by the bulb 54 is concentrated and held in the proximity of the holders 14. More specifically, the housing 58 is designed to fit over the base member 12, and is secured to the base member 12 with suitable fasteners such as the screws 60. An opening 62 is provided in the housing 58 for accessing the receptors 28 of each of the holders 14, and holes 64 are provided for receiving the setscrews 46 such that the knobs 49 are exterior to the housing 58 to allow the setscrews to be actuated while the housing 58 is in place.

Figure 5:
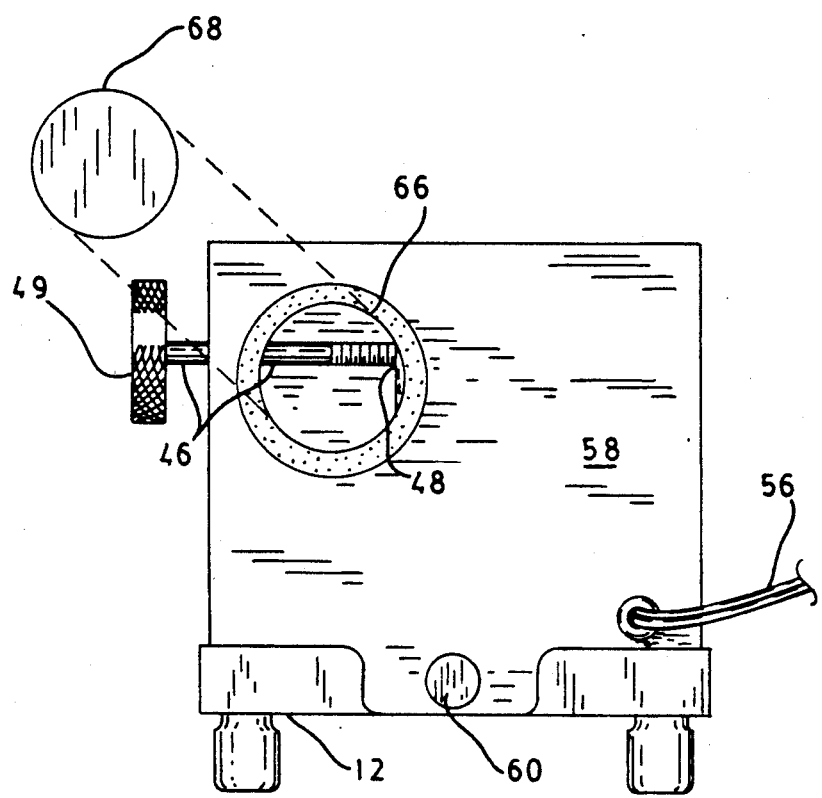
FIG. 5 illustrates a side elevation view of a resheathing device of FIG. 1.

In the preferred embodiment, the housing 58 is fabricated of nylon or other strong elastic polymer. In this regard, nylon possesses the insulating qualities necessary to avoid heat loss, and its surface is less likely to dull a needle point when resheathing is attempted and the receptor 28 is missed. Further, as illustrated in FIG. 5, an opening 66 can be provided in the housing 58 to allow the components within the housing to be viewed without removal of the housing 58. This ability to see within the cover is particularly useful when aligning the setscrews 46 for threaded insertion into the threaded openings 48. As illustrated, a closure or plug 68 is also provided for covering the opening 66 when the opening is not in use such that heat is not lost from the housing.

Figure 7:
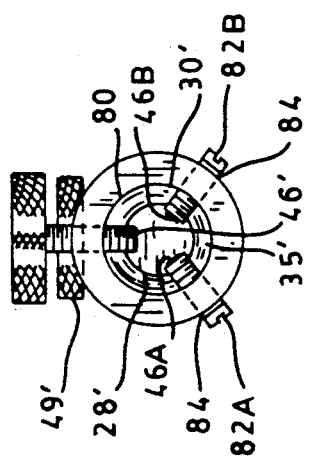
FIG. 7 is a front view of a sheath holder of the type of a resheathing device as shown in FIG. 6, as separate from its support bracket.
Figure 6:
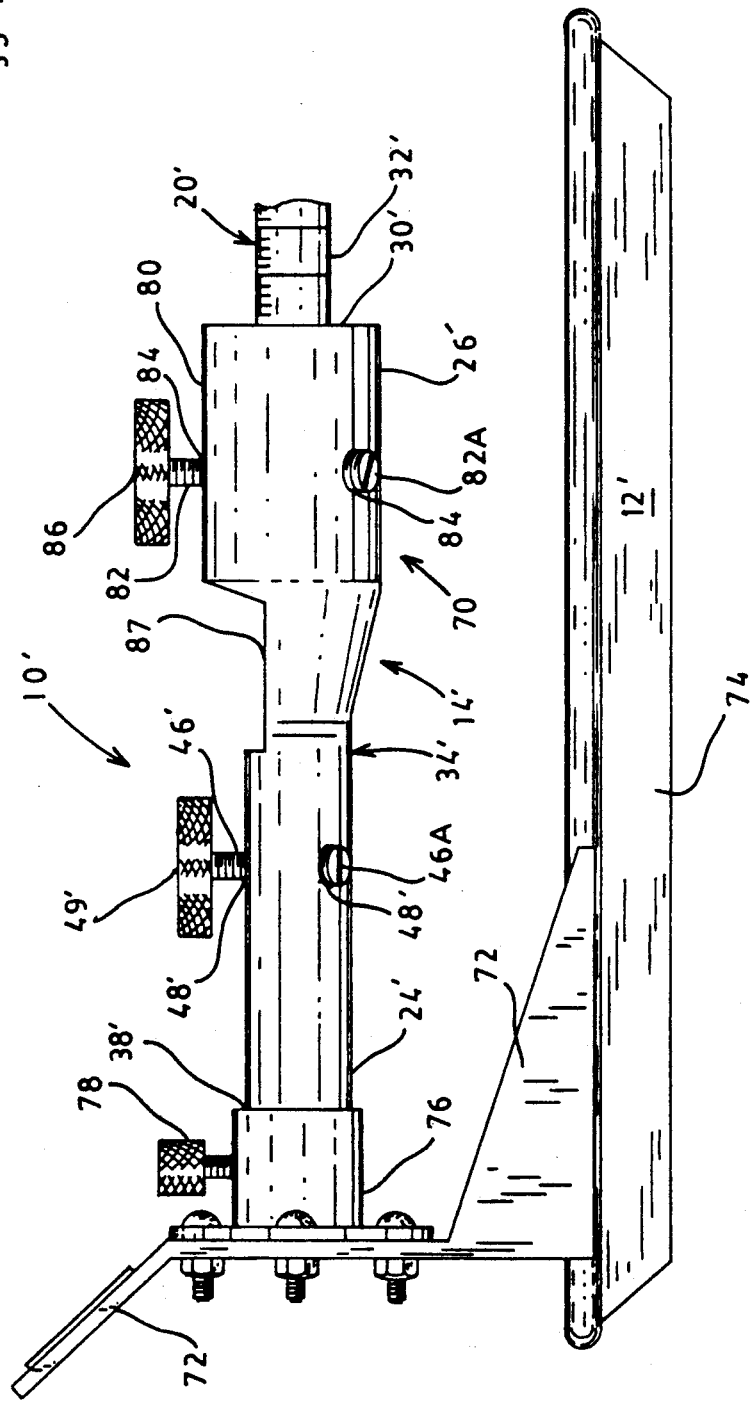
FIG. 6 illustrates a side elevation view of an alternate embodiment of a resheathing device of the present invention.

In FIGS. 6 and 7, an alternate embodiment of the syringe resheathing device of the present invention is illustrated at 10'. As with the device 10 described above, the device 10' generally comprises a base member 12' to which is secured one or more sheath holders 14'. However, as will be discussed in detail below, the device 10' also includes syringe engaging means 70, operatively associated with each sheath holder 14' to allow the device 10' to be transported without the risk of a syringe becoming inadvertently dislodged from its sheath.

Figure 8:
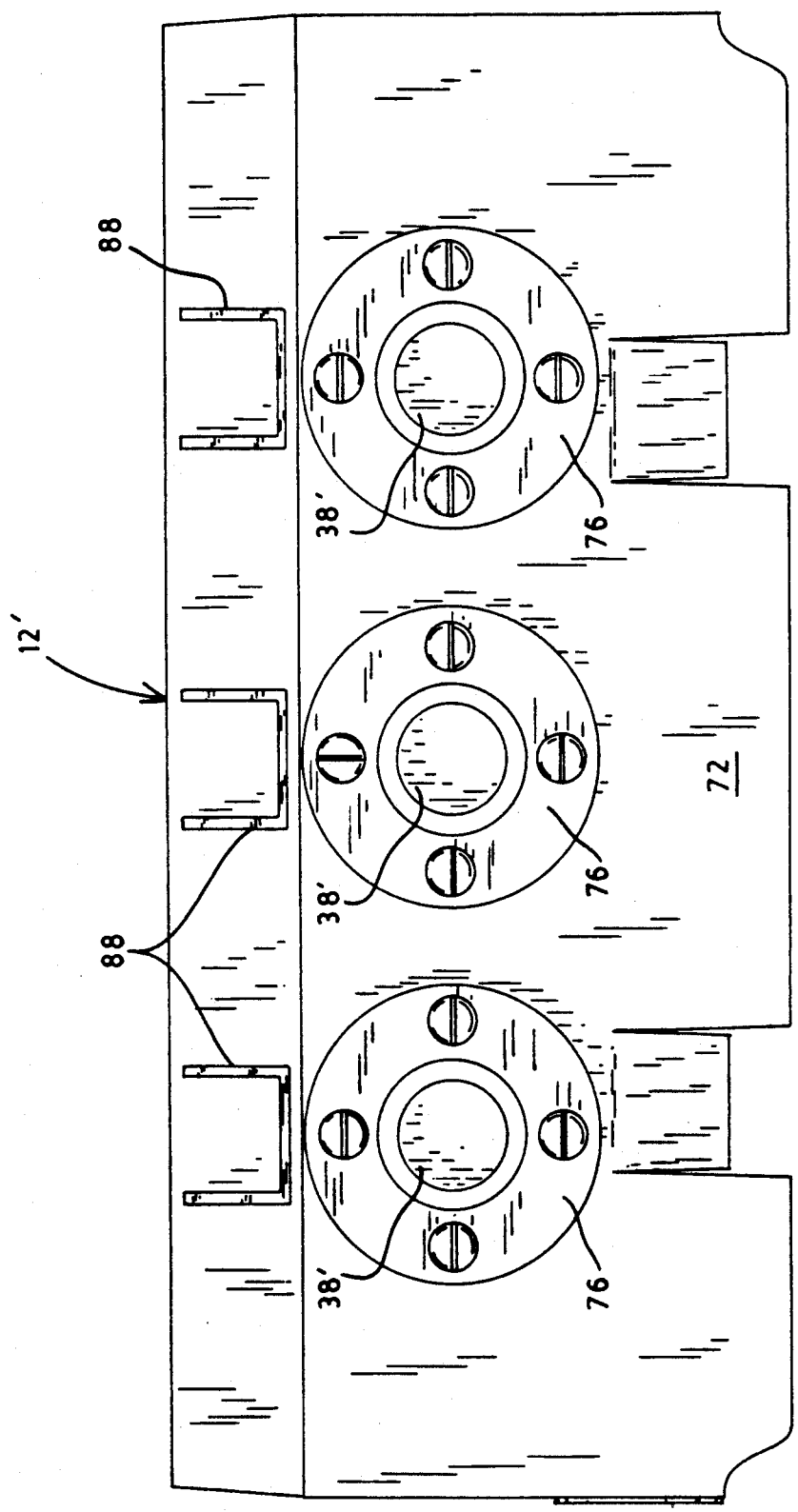
FIG. 8 is a front view of the bracket member of the alternate embodiment of a resheathing device of FIG. 6.

In a preferred form of this alternate embodiment, the base member 12' of the device 10' comprises a bracket member 72 which can be releasably mounted on a medication tray 74, or other support structure (See also FIG. 8). Of course, the bracket member 72 can be more permanently secured to the tray 74, or other structure, by welding or various other fastening means. The base member 12' further comprises one or more mounting members 76 secured to the forward surface of the bracket member 72 for supporting the sheath holders 14'. In this regard, each of the mounting members 76 defines a receptor 38' for receiving the first end portion 24' of a holder 14', and the receptor 38' can be threaded to releasably receive the first end portion 24' of the holder 14', or the holder 14' can be slidably received in the receptor 38' and secured therein with the illustrated set screw 78. However, it will be recognized that other suitable securing means can be used to secure the holder 14 in the mounting members 76, or directly to the bracket member 72. Also, it will be recognized that the sheath holders could penetrate the bracket member so as to be supported from other than the end of each.

Each of the sheath holders 14' comprises a sleeve 34' which includes the syringe engaging means 70 disposed at its second end portion 26'. In this regard, in the preferred embodiment the passageway 35' of the sleeve 34' defines both a sheath receptor 28' and a syringe receptor 80, the syringe receptor 80 defining a greater cross-sectional diameter than the receptor 28' so as to accommodate the larger diameter of the syringe barrel 32'. Accordingly, when the device 10' is used, the sheathed syringe 20 is inserted into the holder 14' through the opening 30' and positioned such that the syringe sheath is received in the receptor 28', and the forward portion of the barrel 32' of the syringe 20 is received in the receptor 80.

Further, locking means are provided both for releasably locking the sheath within the receptor 28' and for releasably locking the syringe in the receptor 80. In a preferred embodiment, the locking means for releasably locking the sheath within the receptor 28' comprises a first setscrew 46' and a pair of further setscrews 46A and 46B. The setscrews 46' and 46A and B are each threadably received by, and through, threaded receptors 48' in the wall of the sleeve 34' and preferably are aligned so as to define axes converging on the axis of the receptor 28'. Accordingly, when a sheath is positioned in the receptor 28', it can be locked in place by threading the setscrews 46', and 46A and B, inwardly to engage the sheath. Of course, it will be appreciated that the position of the setscrews 46A and B can be preset prior to insertion of the sheath such that only the setscrew 46', provided with an actuating knob 49', need by actuated to lock the sheath in place.

Similarly, in this embodiment, the locking means for releasably locking the syringe 20 in the receptor 80 comprises a first setscrew 82 and a pair of further setscrews 82A and 82B. The setscrews 82, and 82A and B, are each threadably received by, and through, a threaded receptor 84 in the wall and are preferably aligned so as to define axes converging on the axis of the receptor 80. Accordingly, when a syringe is positioned in the receptor 80, it can be locked in place by threading the setscrews 82, and 82A and B, inwardly to engage the syringe barrel 32'. As with the setscrews 46A and 46B, the position of the setscrews 82A and B can be preset prior to insertion of the syringe such that only the setscrew 82, provided with an actuator knob 86, need be actuated to lock or unlock the syringe. It will also be noted that the holders 14' can be provided with an opening 87 which allows visual access to the interior of the passageway 35' to allow the necessary depth of insertion of the syringe to be determined to effect proper locking of the sheath and the syringe.

In light of the above, it will be appreciated that the device 10' is ideal not only for safely unsheathing and resheathing a syringe using one hand, but also for safely transporting syringes. For example, a sheathed syringe 20 can be inserted into a holder 14' and the sheath locked into the receptor 28'. The syringe can then be safely unsheathed, filled and resheathed with no danger of inadvertent injection or contact with the needle. The syringe 20 can then be locked in the receptor 80 and the device 10' transported to the patient without risk of the syringe becoming unsheathed. In this regard, the bracket member 72 can be provided with card holders 88 for releasably receiving a card (not shown) carrying information such as the content of the syringe, the patient's name, room number, blood type, etc. The syringe can then be unlocked and withdrawn from the receptor 80, leaving the sheath locked in place in the receptor 28', and the injection administered. Once the injection has been given, the syringe can be resheathed with no risk of contact with the contaminated needle, and the syringe can be locked in the receptor 80 such that it can safely be transported for safe disposal.

While a preferred embodiment has been shown and described, it will be understood that there is no intent to limit the invention to such disclosure, but rather it is intended to cover all modifications and alternate constructions falling within the spirit and scope of the invention as defined in the appended claims.

I claim:

1. A syringe resheathing device for lockably receiving the needle sheath of a hypodermic syringe, said device comprising:
   a base member for being supported on a support surface during use of said device;
   at least one sheath holder, said sheath holder having sidewalls and first and second end portions, said first end portion being secured to said base member whereby said sheath holder is supported by said base member, said second end portion extending outwardly from said base member, said sheath holder sidewalls defining a sheath receptor within said sheath holder for closely receiving said needle sheath of said syringe; and
   locking means extending through said sidewalls of said sheath holder, said locking means having a first end within said receptor for engaging said needle sheath in said sheath receptor, and a second end exterior to said sheath holder for operation of said locking means by a user, whereby said needle sheath is releasably and securely held in said sheath receptor during the unsheathing and resheathing of said syringe by said user using only one hand.

2. The resheathing device of claim 1 wherein said device is provided with a plurality of said sheath holders.

3. The resheathing device of claim 1 wherein said sheath holder comprises a cylindrical sleeve defining said sheath receptor and said first and second end portions, said sleeve further defining an opening at said second end portion for accessing said sheath receptor.

4. The resheathing device of claim 1 wherein said sidewalls of said sheath holder define a threaded opening, and wherein said locking means comprises a first setscrew for being threaded through said threaded opening so as to lockably engage said needle sheath.

5. The resheathing device of claim 3 wherein said sleeve is provided with a threaded opening, and wherein said locking means comprises a first setscrew for being threaded through said threaded opening so as to lockably engage said needle sheath.

6. The resheathing device of claim 3 wherein said base member defines at least one threaded receptor, and wherein said first end portion of said sleeve is threaded so as to be releasably received in said threaded receptor of said base member.

7. The resheathing device of claim 1 wherein said device further comprises heating means for warming said needle sheath of said syringe as said sheath is received in said sheath receptor.

8. The resheathing device of claim 7 wherein said heating means comprises a light bulb socket mounted on said base member for receiving a light bulb, said socket being provided with an electrical cord for connecting said socket to an electrical power source.

9. The resheathing device of claim 8 wherein said device is provided with a housing for being secured on said base member and for housing said sheath holder and said light bulb socket.

10. The resheathing device of claim 1 wherein said sheath holder is provided at its second end portion with syringe engaging means for releasably engaging said syringe, said syringe engaging means including locking means for releasably engaging said syringe when said syringe needle is sheathed in said needle sheath.

11. A device to permit a user of a hypodermic syringe to unsheath and resheath said syringe by removing and replacing the needle sheath of said syringe using only one hand, said device comprising:
   a base member for firmly positioning said device upon a support surface during said removing and replacing of said needle sheath;
   at least one elongated sheath holder attached to said base member, said sheath holder having a circumferential sidewall to define an axial cylindrical sheath receptor to receive said needle sheath, said sheath holder having first and second end portions, said second end portion defining an opening for accessing said sheath receptor, said sidewall provided with an opening oriented radially with respect to the axis of said receptor and extending from an exterior surface of said sheath holder to said sheath receptor; and
   locking means extending through said opening in said sidewall and operable by said user, said locking means having a first end for releasably locking said needle sheath in said receptor, and a second end exterior of said sheath holder for operation by said user, whereby said needle sheath is held securely in said sheath receptor during said removing and replacing of said needle sheath relative to said syringe by said user using only one hand.

12. The device of claim 11 wherein a plurality of said sheath holders are attached to said base member.

13. The device of claim 11 wherein said opening in said sidewall of said sheath holder is threaded, and wherein said locking means is a first setscrew for being threaded through said threaded opening into said sheath receptor so as to lockably engage said needled sheath.

14. The device of claim 11 further comprising a syringe support means at said second end portion of said sheath housing, said syringe support means including engaging means for releasably engaging the barrel of said syringe when the needle of said syringe needle is sheathed in said needle sheath within said sheath receptor to thereby prevent inadvertent removal of said needle from said needle sheath.

15. A syringe resheathing device for lockably receiving the needle sheath of a hypodermic syringe, said device comprising:
- a base member provided with a plurality of threaded receptors;
- a plurality of sheath holders, each said sheath holder including a sleeve defining sidewalls and provided with a passageway therethrough, at least a portion of said passageway defining a sheath receptor, said sleeve having a threaded first end portion for being releasably received in said threaded receptor of said base member, and having a second end portion defining an opening for accessing said sheath receptor, said sleeve being further provided with at least one threaded opening in said sidewalls;
- locking means, operatively associated with said sheath holders, for releasably locking said needle sheath in said sheath receptor, said locking means including at least one setscrew for being received through said threaded opening of said sleeve so as to releasably engage and lock said sheath within said sheath receptor; and
- heating means for warming said needle sheath of said syringe as said sheath is received in said sheath receptor, said heating means including a light bulb socket mounted on said base member for receiving a light bulb, said socket being provided with an electrical cord for connecting said socket to an electrical power source.

16. The resheathing device of claim 15 wherein at least one said sheath holder is provided with at least one spacer member for being slidably received in said passageway of said sheath, said spacer member having an upper surface for defining the bottom of said sheath receptor as said spacer member is received in said passageway.

17. The resheathing device of claim 15 wherein said device is provided with a housing for being secured on said base member and for housing said sheath holder and said light blub socket.

18. A syringe resheathing device for lockably receiving the needle sheath of a hypodermic syringe, and for lockably engaging said syringe, said device comprising:
- a base member;
- at least one sheath holder, said sheath holder including a sleeve defining sidewalls and provided with a passageway therethrough, at least a portion of said passageway defining a sheath receptor and a portion of said passageway defining a syringe receptor, said sleeve having a first end portion for engaging said base member and a second end portion defining an opening for accessing said syringe receptor and said sheath receptor, said syringe receptor being defined proximate said second end portion of said sleeve and said sheath receptor being defined between said syringe receptor and said first end portion of said sleeve, whereby said needle sheath is releasably received in said sheath receptor and said syringe is releasably received in said syringe receptor as said syringe receptor is sheathed in said needle sheath, said sleeve further defining at least one threaded opening communicating with said sheath receptor, and at least one second threaded opening communicating with said syringe receptor;
- locking means for releasably securing said needle sheath in said sheath receptor, said locking means including at least one setscrew for being threadably received through said first threaded opening of said sleeve and releasably engaging said needle sheath; and
- locking means for releasably securing said syringe in said syringe receptor, said locking means comprising at least one second setscrew for being threadably received through said second threaded opening of said sleeve so as to releasably engage said syringe.

19. The resheathing device of claim 18 wherein said sleeve comprises a plurality of said first threaded openings radially disposed relative to the axis of said sleeve, and a plurality of said second threaded openings radially disposed relative to the axis of said sleeve, and wherein said means for releasably securing said needle sheath in said sheath receptor comprises a plurality of said first setscrews, and said means for releasably securing said syringe in said syringe receptor comprises a plurality of said second setscrews.

20. The resheathing device of claim 18 wherein said base member comprises a bracket member for mounting on a transportable support structure.

* * * * *

UNITED STATES PATENT AND TRADEMARK OFFICE
CERTIFICATE OF CORRECTION

PATENT NO.   : 5,013,299

DATED        : May 7, 1991

INVENTOR(S)  : William C. Clark

It is certified that error appears in the above-identified patent and that said Letters Patent is hereby corrected as shown below:

Col. 2, line 7   "particular" should read --particularly--.
Col. 2, line 17  "an" should read --and--.
Col. 6, line 47  "by" should read --be--.
Col. 8, line 60  "needled" should read --needle--.
Col. 9, line 33  "sheath" should read --sheath holder--.
Col. 9, line 40  "blub" should read --bulb--.

Signed and Sealed this

Twenty-ninth Day of December, 1992

Attest:

DOUGLAS B. COMER

Attesting Officer

Acting Commissioner of Patents and Trademarks